United States Patent [19]
Easton et al.

[11] 3,994,917
[45] Nov. 30, 1976

[54] OXAZOLINIUM SALT PROCESS

[75] Inventors: Nelson R. Easton; William W. Hargrove, both of Indianapolis, Ind.

[73] Assignee: Eli Lilly and Company, Indianapolis, Ind.

[22] Filed: Mar. 10, 1975

[21] Appl. No.: 556,766

Related U.S. Application Data

[63] Continuation-in-part of Ser. No. 827,043, May 22, 1969, which is a continuation-in-part of Ser. No. 502,359, Oct. 22, 1965, abandoned.

[52] U.S. Cl. .................. 260/307 F; 260/239 A; 260/557 R; 260/558 R; 260/558 D; 260/558 P; 260/561 R; 260/562 R; 260/562 P; 260/563 C; 260/563 P; 260/570.5 CA; 260/570.5 C; 260/576; 260/584 A; 260/563 R; 424/244

[51] Int. Cl.² .................................. C07D 263/32
[58] Field of Search ........................... 260/307 F

[56] References Cited
UNITED STATES PATENTS

| | | | |
|---|---|---|---|
| 3,278,544 | 10/1966 | Easton | 260/307 |
| 3,481,920 | 12/1969 | Hargrove | 260/239 |

*Primary Examiner*—Raymond V. Rush
*Attorney, Agent, or Firm*—James L. Rowe; Everet F. Smith

[57] ABSTRACT

A novel process for preparing oxazolinium salts useful in the preparation of $\alpha'$-halo $\alpha,\alpha$-disubstituted $\alpha$-amino ketones.

4 Claims, No Drawings

OXAZOLINIUM SALT PROCESS

CROSS-REFERENCE co-pending

This application is a continuation-in-part of our co-pending application, Ser. No. 827,043 filed May 22, 1969 which application was in turn a continuation-in-part of our then co-pending application, Ser. No. 502,359, filed Oct. 22, 1965, now abandoned.

BACKGROUND OF THE INVENTION $\alpha'$-Halo $\alpha,\alpha$-disubstituted $\alpha$-amino ketones are useful as intermediates in the synthesis of $\alpha,\alpha$-disubstituted azetidonones, as set forth in the co-pending applications of William W. Hargrove, Ser. No. 502,331 filed Oct. 22, 1965, now U.S. Pat. No. 3,481,920 issued Dec. 2, 1969 and Ser. No. 790,852, filed Jan. 13, 1969, now U.S. Pat. No. 3,494,964 issued Feb. 10, 1970.

A synthesis of $\alpha'$-halo $\alpha,\alpha$-disubstituted $\alpha$-amino ketones is described in U. S. Pat. No. 3,481,920. According to this synthesis the desired product is obtained by treating a glacial acetic acid solution of the amino ketone with the appropriate halogen. The product is isolated in the form of the acid addition salt of Formula I. This simple convenient, and easily performed preparation has been found to possess certain limitations, e.g., in those compounds where $R^3$ represents a monophenyl-substituted lower alkyl group, halogenation appears to occur in the alkyl portion of said group.

It is an object of this invention to provide a method of obtaining $\alpha'$-halo $\alpha,\alpha$-disubstituted $\alpha$-amino ketones, which method avoids the undesirable aspects of previous methods.

SUMMARY

This invention relates to a novel process for preparing $\alpha'$-halo $\alpha,\alpha$-disubstituted $\alpha$-amino ketones and to intermediates useful in that process.

The novel process provided by this invention comprises the halogenation of an acylamidoacetylene in an inert solvent to yield an oxazolinium derivative. Treatment of the oxazolinium salt with water produces directly the enolate of an $\alpha'$-halo $\alpha,\alpha$-disubstituted $\alpha$-amino ketone, which enolate, upon treatment with acid, ketonizes to yield the desired $\alpha'$-halo $\alpha,\alpha$-disubstituted $\alpha$-amino ketone. This process is more graphically illustrated with reference to Reaction Sequence I below.

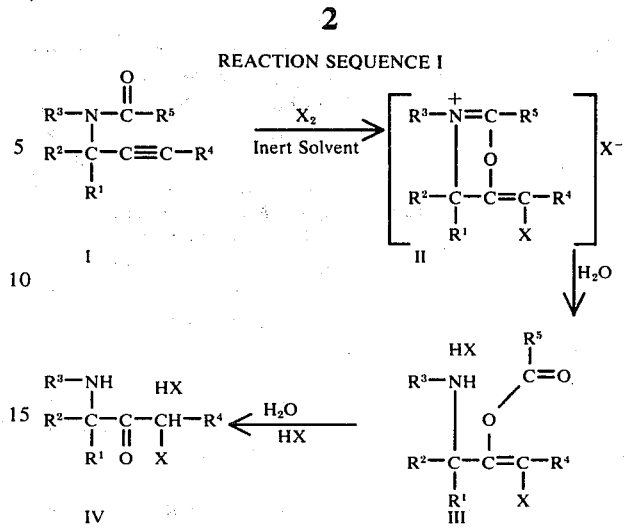

REACTION SEQUENCE I wherein
$R^1$ and $R^2$, when taken separately, are $C_1$–$C_5$ alkyl, $C_5$–$C_6$ cycloalkyl, or phenyl;
$R^1$ and $R^2$, when taken together with the carbon atom to which they are attached, represent $C_5$–$C_6$ cycloalkyl;
$R^3$ is hydrogen, $C_1$–$C_5$ alkyl, $C_4$–$C_8$ cycloalkyl, phenyl, or phenyl-substituted $C_1$–$C_3$ alkyl;
$R^4$ is hydrogen or $C_1$–$C_3$ alkyl;
$R^5$ is $C_1$–$C_5$ alkyl, $C_5$–$C_6$ cycloalkyl, phenyl, halo-substituted phenyl or phenyl-substituted $C_1$–$C_3$ alkyl; and
X is bromine, chlorine, or iodine.

In the above formulas, "$C_1$–$C_5$ alkyl" can be illustratively methyl, ethyl, isopropyl, n-propyl, sec.-amyl, sec.-butyl, t-butyl, n-amyl, isobutyl, isoamyl, 3-methyl-2-butyl, 2-methyl-2-butyl, 2-pentyl, 3-pentyl, neopentyl, and the like.

"$C_5$–$C_6$ cycloalkyl" can be cyclohexyl or cyclopentyl.

"$C_4$–$C_8$ cycloalkyl" can be illustratively cyclobutyl, cyclopentyl, cyclohexyl, cycloheptyl, cyclo-octyl, methyl-cyclopentyl, ethylcyclohexyl, and the like.

"$C_1$–$C_3$ alkyl" can be methyl, ethyl, n-propyl, and isopropyl.

Representative "phenyl-substituted $C_1$–$C_3$ alkyl" radicals are benzyl, 2-phenethyl, 2-phenylpropyl, 3-phenylpropyl, 1-phenylethyl, and the like.

The term "halo-substituted phenyl" includes a phenyl radical substituted with one or more halogen atoms such as o-chlorophenyl, p-iodophenyl, m-fluorophenyl, 2-chloro-4-bromophenyl, 2,4,5-trichlorophenyl, and the like.

According to the novel process of the instant invention, a solution of acylamido acetylene (I) in an inert solvent is treated with the desired halogen. Suitable inert solvents include chloroform, ether, dioxane, methylene dichloride, dichloroethane, dimethylformamide, and the like. The halogenation reaction is spontaneous, the reaction mixture becoming warm, and the halogen color disappearing without the necessity of external heating. Some of the oxazolinium salts (II) thus formed are sufficiently insoluble in the reaction mixture to precipitate immediately as the reaction proceeds and can be conveniently recovered by filtration. Others are more soluble, and it is necessary to concentrate the reaction mixtures in order to cause the oxazolinium salt to precipitate. The structures of the oxazolinium salts have been determined and assigned through the use of elemental analyses and infrared and nuclear magnetic resonance (n.m.r.) spectra.

Conversion of the oxazolinium salts to the enol esters, (III) is accomplished by treating the oxazolinium salt with a mixture of acetone and water, concentrating the reaction mixture to dryness, and recrystallizing the residue from a suitable solvent. However, in some cases the oxazolinium salt is sufficiently unstable to undergo rapid conversion to the enol ester merely on standing. Structures of these enol esters have also been confirmed by elemental and spectral analysis.

Hydrolysis of the enol esters using strong acids in aqueous solution yields the desired $\alpha'$-halo $\alpha,\alpha$-disubstituted $\alpha$-amino ketones, which are obtained in the form of their acid addition salts. Strong acids suitable for use in this hydrolysis include hydrochloric, hydrobromic, and hydriodic acids.

The acylamido acetylenes (I) wherein $R^1$ and $R^2$ are $C_1$–$C_5$ alkyl employed as starting materials in our novel process can be prepared by the method of Easton et al., *J. Org. Chem.* 28, 2465 (1963), utilizing aminoacetylenes synthesized by the methods of Hennion and Hanzel, *J. Am. Chem. Soc.* 82, 4908 (1960), or of Easton et al., *J. Org. Chem.* 26, 3772 (1961). Starting materials wherein $R^1$ or $R^2$ is phenyl are prepared by the process described in Easton et al. in *J. Org. Chem.* 27, 2746 (1962).

The $\alpha'$-halo $\alpha,\alpha$-disubstituted $\alpha$-amino ketones preparable by the process of this invention are useful intermediates in the preparation of 2,2-disubstituted-3-azetidinones, which compounds are disclosed in the co-pending application of William W. Hargrove, U.S. Pat. No. 3,481,920 issued Dec. 2, 1969. These latter 3-azetidinones have interesting hypotensive activity. In addition, they serve as intermediates in the preparation of the corresponding 3-azetidinols and azetidines. The azetidinols possess CNS stimulant properties and the azetidines are blood pressure-lowering agents. The hypotensive properties of the 3-azetidinones preparable from the compounds of this invention can be utilized by administering 3-azetidinones in a composition adapted for oral or parenteral administration, oral administration being especially preferred because of the ease and convenience associated therewith. Thus, the 3-azetidinones can be administered in the form of a compressed tablet or a filled capsule, as well as in the form of a solution or suspension suitable for oral or intramuscular administration. The hypotensive activity of the 3-azetidinones is shown when they are administered orally to rats made hypertensive by the well-known Goldblatt method. Doses of 20–40 mg./kg. orally cause a significant lowering of the blood pressure in the test animals.

The 3-azetidinols and azetidines preparable from the said 3-azetidinones possessing CNS stimulant properties can be utilized by administration in a form adapted for intra-peritoneal administration. Thus, they can be in the form of a solution or suspension suitable for intra-peritoneal administration. The CNS stimulant properties are shown when the compounds are administered intra-peritoneally to mice in doses of 10–100 mg./kg. These dosages produce an increase in the rate of respiration, some vasodilatation, and an increased irritability of the test animals.

The oxazolinium salts and enol ester acid addition salts, Formulas II and III, respectively, are useful intermediates in the preparation of the above $\alpha'$-halo $\alpha,\alpha$-disubstituted $\alpha$-amino ketones preparable by the process of this invention.

The invention is more clearly described by the following operating examples, which are not intended to limit the scope thereof in any way.

EXAMPLE 1

2,3,4,4-Tetramethyl-5-(bromomethylene)-2-oxazolinium bromide

A solution of 20 g. of 3-methyl-3-(N-acetyl-N-methyl)-amino-1-butyne in 200 ml. of chloroform was treated with 23 g. of bromine dissolved in 50 ml. of chloroform. The solid which separated was filtered off and recrystallized from isopropyl alcohol to yield 38 g. of 2,3,4,4-tetramethyl-5-(bromomethylene)-2-oxazolinium bromide having a melting point of about 225°–227° C. It was identified by elemental analysis and by infrared and n.m.r. sprectra.

Analysis. Calcd: C, 32.13; H, 4.38. Found: C, 32.37; H, 4.49.

Using the same procedure as described in Example 1, the following compounds were prepared:

2,4,4-Trimethyl-5-(bromomethylene)-2-oxazolinium bromide. Melting Point: 188°–190° C.

Analysis. Calcd. C, 29.50; H, 3.89. Found: C, 29.64; H, 3.89.

2-(p-Chlorophenyl)-3,4,4-trimethyl-5-(1-bromoethylidene)-2-oxazolinium bromide. Melting point: 225°–227° C.

Analysis. Calcd: C, 41.05; H, 3.93. Found: C, 41.00; H, 4.20.

2-(3,4-Dichlorophenyl)-3-methyl-4,4-pentamethylene-5-(bromomethylene)-2-oxazolinium bromide. Melting Point: 233°–234° C.

2-(2,4-Dichlorophenyl)-4,4-pentamethylene-5-(bromomethylene)-2-oxazolinium bromide. Melting point: 128°–129° C.

Analysis. Calcd: C, 39.50; H, 3.31. Found: C, 39.10; H, 3.48.

2,3,4,4-Tetramethyl-5-(chloromethylene)-2-oxazolinium chloride was obtained and identified by means of infrared and n.m.r. spectra.

3,4,4-Trimethyl-5-(chloromethylene)-2-oxazolinium chloride. Melting point: 162°–164° C. Identified by means of infrared and n.m.r. spectra.

2,3,4,4-Tetramethyl-5-(1-bromoethylidene)-2-oxazolinium bromide. Melting point: 219°–221° C.

Analysis. Calcd: C, 34.53; H, 4.82. Found: C, 34.40; H, 4.76.

2,3-Dimethyl-4,4-pentamethylene-5-(bromomethylene)-2-oxazolinium bromide. Melting point: 206°–208° C.

Analysis. Calcd: C, 38.96; H, 5.05. Found: C, 38.82; H, 5.60.

3,4,4-Trimethyl-5-(bromomethylene)-2-oxazolinium bromide. Melting point: 205°–206° C. with decomposition.

Analysis. Calcd: C, 29.50; H, 3.89. Found: C, 29.39; H, 4.18.

2,4-Dimethyl-4-sec.-butyl-5-(bromomethylene)-2-oxazolinium bromide. Melting point: 190°–200° C. with decomposition.

Analysis. Calcd: C, 36.72; H, 5.23. Found: C, 36.29; H, 5.36.

2,4-Dimethyl-4-isopropyl-5-(bromomethylene)-2-oxazolinium bromide. Melting point: 187°–189° C. with decomposition.

Analysis. Calcd: C, 34.53; H, 4.82. Found: C, 34.71; H, 5.05.

2-(3,4-Dichlorophenyl)-3,4,4-trimethyl-5-(bromomethylene)-2-oxazolinium bromide. Melting point: 240°–241° C.

Analysis. Calcd: C, 36.31; H, 3.04. Found: C, 42.23; H, 4.34.

2-(p-Chlorophenyl)-3,4,4-trimethyl-5-(iodomethylene)-2-oxazolinium iodide. Melting point: 214°–216° C.

Analysis. Calcd: C, 31.89; H, 2.88. Found: C, 32.07; H, 2.80.

EXAMPLE 2

1-Chloro-N,3-dimethyl-2-(2,4-dichlorobenzoyloxy)-1-butenyl-3-amine hydrochloride To a solution of 10 g. of 3-(N-methyl-2,4-dichlorobenzamido)-3-methyl-1-butyne in chloroform was added a solution of 10 g. of chlorine in chloroform dropwise until a yellowish color persisted. The solution was evaporated to dryness in vacuo and the residue recrystallized from ethyl acetate to yield 1-chloro-N,3-dimethyl-2-(2,4-dichlorobenzoyloxy)-1-butenyl-3-amine hydrochloride in the form of a solid having a melting point of about 198°–199° C.

Analysis. Calcd: C, 43.48; H, 4.21. Found: C, 43.30; H, 4.32.

Using the same procedure as described in Example 2, the following compounds were prepared:

1-[2-Chloro-1-(2,4-dichlorobenzoyloxy)vinyl]-N-methylcyclohexylamine hydrochloride. Melting point: 116°–117° C.

Analysis. Calcd: C, 48.14; H, 4.80. Found: C, 47.61; H, 4.84.

1[2-Chloro-1-(3,4-dichlorobenzoyloxy)vinyl]-N-methylcyclohexylamine hydrochloride. Melting point: 197°–198° C.

Analysis. Calcd: C, 48.14; H, 4.80. Found: C, 48.49; H, 4.65.

1-[2-Chloro-1-(p-chlorobenzoyloxy)vinyl]-N-methylcyclohexylamine hydrochloride. Melting point: 95°–96° C.

Analysis. Calcd: C, 52.98; H, 5.00. Found: C, 52.93; H, 5.16.

1-Bromo-N,3-dimethyl-2-(p-chlorobenzoyloxy)-1-butenyl-3-amine-hydrobromide. Melting point: 194°–196° C.

Analysis. Calcd: C, 37.75; H, 3.90. Found: C, 38.11; H, 4.12.

1-Bromo-N,3-dimethyl-2-(2,4-dichlorobenzoyloxy)-1-butenyl-3-amine hydrobromide. Melting point: 162°–163° C.

Analysis. Calcd: C, 34.85; H, 3.37. Found: C, 34.95; H, 3.26.

1-[2-Bromo-1-(2,4-dichlorobenzoyloxy)vinyl]-N-methylcyclohexylamine hydrobromide. Melting point: 174°–175° C.

Analysis. Calcd: C, 39.37; H, 3.92. Found: C, 39.29; H, 4.17.

EXAMPLE 3

1-Bromo-N,3-dimethyl-2-(3,4-dichlorobenzoyloxy)-1-butenyl-3-amine hydrobromide 5 g. of 2-(3,4-dichlorophenyl)-3,4,4-trimethyl-5-bromomethylene-2-oxazolinium bromide were dissolved in a mixture of 100 ml. of acetone and 1.0 ml. of water. The solution was evaporated in vacuo and the residue recrystallized from methyl ethyl ketone to yield 5 g. of 1-bromo-N,3-dimethyl-2-(3,4-dichlorobenzoyloxy)-1-butenyl-3-amine hydrobromide having a melting point of about 180° C. (dec.).

Analysis. Calcd: C, 34.85; H, 3.37. Found: C, 35.06; H, 3.67.

Additional compounds prepared by the above procedure include:

1-[1-(3,4-Dichlorobenzoyloxy)-2-bromovinyl]-N-methylcyclohexylamine hydrobromide. Melting point: 182° C. (dec.).

Analysis. Calcd: C, 39.37; H, 3.92. Found: C, 39.11; H, 4.04.

1-[1-(2,4-Dichlorobenzoyloxy)-2-bromovinyl]-N-methylcyclohexylamine hydrobromide. Melting point: 162°–163° C.

Analysis. Calcd: C, 39.37; H, 3.92. Found: C, 39.41; H, 4.07.

1-Bromo-N,3-dimethyl-2-(2,4-dichlorobenzoyloxy)-1-butenyl-3-amine hydrobromide. Melting point: 180° C. (dec.).

Analysis. Calcd: C, 34.85; H, 3.37. Found: C, 34.95; H, 3.26.

1-Chloro-N,3-dimethyl-2-(2,4-dichlorobenzoyloxy)-1-butenyl-3-amine hydrochloride. Melting point: 198°–199° C.

Analysis. Calcd: C, 43.48; H, 4.21. Found: C, 43.30; H, 4.23.

1-[1-(2,4-Dichlorobenzoyloxy)-1-chlorovinyl]-N-methylcyclohexylamine hydrochloride. Melting point: 116°–117° C.

Analysis. Calcd: C, 48.14; H, 4.80. Found: C, 47.61; H, 4.84.

1-[1-(3,4-Dichlorobenzoyloxy)-1-chlorovinyl]-N-methylcyclohexylamine hydrochloride. Melting point: 197°–198° C.

Analysis. Calcd: C, 48.14; H, 4.80. Found: C, 48.49; H, 4.65.

1-Bromo-N,3-dimethyl-2-(3,4-dichlorobenzoyloxy)-1-butenyl-3-amine hydrobromide. Melting point: 180° C. (dec.).

Analysis. Calcd: C, 34.85; H, 3.37. Found: C, 35.06; H, 3.67.

1-[2-Bromo-1-(3,4-dichlorobenzoyloxy)vinyl]-N-methylcyclohexylamine hydrobromide. Melting point: 182° C. (dec.).

Analysis. Calcd: C, 39.37; H, 3.92. Found: C, 39.11; H, 4.04.

EXAMPLE 4

1-Bromo-3,4-dimethyl-3-amino-2-pentanone hydrobromide

A solution was prepared of 2,4-dimethyl-4-isopropyl-5-(bromomethylene)-2-oxazolinium bromide in ethanol and allowed to stand at room temperature. The solvent gradually evaporated and the solid residue was recrystallized from ethanol to yield 1-bromo-3,4-dimethyl-3-amino-2-pentanone hydrobromide having a melting point of about 158°–160° C. The material was identified by the n.m.r. spectrum.

EXAMPLE 5

3-Methyl-3-(β-phenethylamino)-1-bromo-2-butanone hydrobromide

A solution of 10 g. of 3-methyl-3-(N-formyl-N-β-phenethyl)amino-1-butyne in 100 ml. of chloroform was prepared, and to the solution were added 100 ml.

of methanol and 8 g. of bromine in chloroform dropwise with stirring. After addition was complete, the solvent was removed in vacuo and the residual oil was dissolved in isopropanol. The solid product which crystallized out was identified as 3-methyl-3-($\beta$-phenethylamino)-1-bromo-2-butanone hydrobromide, a solid having a melting point of about 162°–163° C. with decomposition. The analysis indicates the crystalline compound obtained to be an alcoholate composed of one mole of the amino ketone plus one mole of isopropanol.

Analysis. Calcd: C, 45.19; H, 4.60. Found: C, 45.17; H, 4.80.

EXAMPLE 6

1-Chloroacetyl-N-methylcyclohexylamine

A solution was prepared of 20 g. of 3-pentamethylene-3-(N-methyl-N-formyl)-1-propyne in a mixture of chloroform and ether. Gaseous chlorine was bubbled into the mixture until no more solid was formed. During the introduction of the chlorine gas, the mixture became warm and quite viscous, and more chloroform was added to facilitate stirring.

The excess solvent was removed at reduced pressure and the residual solid recrystallized from a mixture of isopropyl alcohol and ether, to yield 1-chloroacetyl-N-methylcyclohexylamine hydrochloride as a solid having a melting point of about 152°–154° C. The compound was identified by means of the n.m.r. spectrum and elemental analysis.

Analysis. Calcd: C, 47.80; H, 7.57. Found: C, 48.60; H, 7.73.

EXAMPLE 7

2-Methyl-4,4-pentamethylene-5-bromomethylene-2-oxazolinium bromide

To a solution of 66 g. of 3-pentamethylene-3-(N-acetyl)-1-propyne in 100 ml. of dimethylformamide was added a solution of 30 g. of silver nitrate in 50 ml. of dimethylformamide and the mixture stirred for about 3 hours at a temperature of about 60°–80° C. The reaction product mixture was cooled and diluted with saturated aqueous sodium chloride solution and extracted with methylene dichloride. The organic layer was separated, washed with water, dried, and distilled to yield material having a boiling point of about 65° C. at 3 mm. The material was identified by n.m.r. as 2-methyl-4,4-pentamethylene-5-methylene-2-oxazole and was used without further purification in the succeeding step of the preparation.

The crude product from above, 16.5 g., was dissolved in 500 ml. of anhydrous methylene dichloride and maintained under a nitrogen atmosphere while 5.5 ml. of bromine was added dropwise to the solution until the bromine color no longer disappeared. The reaction product mixture was maintained in a nitrogen atmosphere and stirred at ambient room temperature over the weekend. After about one and one-half hours, a solid crystalline product began to appear. The reaction product mixture was filtered and the solid material, which had a melting point of about 198°–204° C. with decomposition, was identified by its elemental analysis and infrared and n.m.r. spectra as 2-methyl-4,4-pentamethylene-5-bromomethylene-2-oxazolinium bromide.

Analysis. Calcd: C, 36.95; H, 4.65; N, 4.31. Found: C, 37.05; H, 4.61; N, 4.32.

Following the above procedures:

N-benzoyl-N-phenethyl 3-amino-3-methyl butyne can be chlorinated to yield 2-phenyl-3-phenethyl-4,4-dimethyl-5-chloromethylene oxazolinium chloride. Reaction of this latter compound with water yields 1-chloro-N-phenethyl-3-methyl-2-benzoyloxy-3-amino-1-butene hydrochloride, treatment of which with acid gives 3-phenethylamino-3-methyl-1-chloro-2-butanone.

N-formyl-N-(2-pentyl)-1-amino-1-ethinylcyclopentane can be brominated to yield 3-(1-pentyl)-4,4-tetramethylene-5-bromomethylene oxazolinium bromide. Reaction of this latter compound with water yields 1-(1-formyloxy-2-chlorovinyl)-1-(2-pentylamino)-cyclopentane hydrobromide, treatment of which with acid gives 1-($\omega$-bromoacetyl)-1-methylamino cyclopentane.

N-2,4-difluorobenzoyl-N-n-butyl-4-amino-4-ethyl-2-hexyne can be iodinated to yield 2-(2,4-difluorophenyl)-3-n-butyl-4,4-diethyl-5-iodoethylidene oxazolinium iodide. Reaction of this latter compound with water yields 1-iodo-N-n-butyl-2-(2,4-difluorobenzoyloxy)-4-ethyl-4-amino-2-hexene hydroiodide, treatment of which with acid yields 4-n-butylamino-4-ethyl-2-iodo-3-hexanone.

Other halo amino ketone preparable by the processes of this invention include:

3-methyl-3-methylamino-1-bromo-2-butanone
3-methyl-3-methylamino-1-chloro-2-pentanone
3-methyl-3-n-propylamino-1-chloro-2-pentanone
1-bromoacetyl-N-methylcyclohexylamine hydrobromide
3-methyl-3-ethylamino-1-bromo-2-pentanone
3-methyl-3-ethylamino-1-chloro-2-n-heptanone hydrochloride
4-ethyl-4-n-butylamino-2-bromo-3-n-heptanone
3-phenyl-3-(phenethylamino)-1-bromo-2-butanone
3-phenyl-3-(phenylamino)-1-bromo-2-butanone
4-phenyl-4-phenylamino-2-bromo-3-hexanone
3-ethyl-3-cyclohexylamino-1-chloro-2-pentanone
4-methyl-3-cyclopropylamino-2-bromo-3-heptanone
1-iodoacetyl-N-methylcyclohexylamine hydriodide Other oxazolinium salts preparable by the processes of this invention and useful as intermediates therein include:

2-(m-bromophenyl)-3-(1-pentyl)-4-cyclopentyl-4-phenyl-5-chloromethylene oxazolinium chloride
2,3-dicyclohexyl-4,4-diphenyl-5-chloropropylidene oxazolinium chloride
2-(3-m-bromophenylpropyl)-3-n-propyl-4,4-di-n-propyl-5-bromomethylene oxazolinium bromide
2-cyclopentyl-3-cyclobutyl-4-phenyl-4-methyl-5-iodomethylene oxazolinium iodide
2-n-butyl-3-(2-phenylpropyl)-4-methyl-4-cyclopentyl-5-(1-iodoethylidene)oxazolinium iodide
3-cyclooctyl-4-methyl-4-isopropyl-5-bromopropylidene oxazolinium bromide.

Other enolacylates of $\alpha$-amino ketones useful as intermediates in the processes of this invention include:

3-chloro-5-(m-bromophenylamino)-5-phenyl-5-cyclopentyl-4-n-caproyloxy-3-pentene
1-chloro-3-cyclohexylamino-3,3-di-phenyl-2-cyclohexylcarboxy-1-propene
N-(3-m-bromophenylpropyl)-3-amino-3-n-propyl-2-n-butyroxy-1-hexene
1-iodo-3-cyclopentylamino-3-phenyl-2-cyclopentylcarboxy-1-butene 2-iodo-4-n-butylamino-4-cyclopentyl-3-(2-phenyl-propionoxy)-2-pentene
3-iodo-5-amino-5,6-dimethyl-4-cyclooctylcarboxy-3-heptene.

We claim:
1. A process for preparing oxazolinium salts which consists essentially of contacting with a halogen, $X_2$, of the group consisting of chlorine, bromine and iodine, in an inert mutual solvent an acylamidoacetylene of the formula:

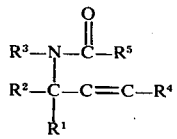

wherein
$R^1$ and $R^2$, when taken separately, are $C_1$–$C_3$ alkyl, $C_5$–$C_6$ cycloalkyl, or phenyl;
$R^1$ and $R^2$, when taken together with the carbon atom to which they are attached, represent $C_5$–$C_6$ cycloalkyl;
$R^3$ is hydrogen, $C_1$–$C_5$ alkyl, $C_5$–$C_6$ cycloalkyl, phenyl, or monophenyl-substituted $C_1$–$C_3$ alkyl;
$R^4$ is hydrogen or $C_1$–$C_3$ alkyl;
$R^5$ is hydrogen, $C_1$–$C_5$ alkyl, halo-substituted phenyl, $C_5$–$C_6$ cycloalkyl or monophenyl-substituted $C_1$–$C_3$ alkyl, and X is bromine, chlorine or iodine; to form an oxazolinium salt of the formula:

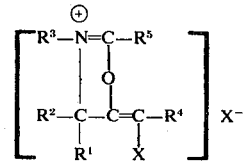

wherein $R^1$, $R^2$, $R^3$, $R^4$, $R^5$, and X have the same meaning as hereinabove.

2. The process which consists essentially of contacting N-(2,4-dichlorobenzoyl) 1-amino-1-ethynylcyclohexane with bromine in an inert mutual solvent to form 2-(2,4-dichlorophenyl)-4,4-pentamethylene-5-(bromomethylene)-2-oxazolinium bromide.

3. The process which consists essentially of contacting N-(p-chlorobenzoyl) 4-methyl-4-methylamino-2-pentyne with bromine in an inert mutual solvent to form 2-(p-chlorophenyl)-3,4,4-trimethyl-5-(1-bromoethylidene)-2-oxazolinium bromide.

4. The process which consists essentially of contacting N-(p-chlorobenzoyl)-3-methyl-3-methylamino-1-butyne with iodine in an inert mutual solvent to form 2-(p-chlorophenyl)-3,4,4-trimethyl-5-(iodomethylene)-2-oxazolinium iodide.

* * * * *